US012751686B2

(12) United States Patent
Takamiya et al.

(10) Patent No.: US 12,751,686 B2
(45) Date of Patent: Oct. 6, 2026

(54) RADIOGRAPHIC IMAGING APPARATUS AND RADIOGRAPHIC IMAGING SYSTEM

(71) Applicant: KONICA MINOLTA, INC., Tokyo (JP)

(72) Inventors: Kiichi Takamiya, Hino (JP); Keisuke Koeda, Tokorozawa (JP)

(73) Assignee: KONICA MINOLTA, INC., Tokyo (JP)

( * ) Notice: Subject to any disclaimer, the term of this patent is extended or adjusted under 35 U.S.C. 154(b) by 206 days.

(21) Appl. No.: 18/635,184

(22) Filed: Apr. 15, 2024

(65) Prior Publication Data

US 2024/0385341 A1 Nov. 21, 2024

(30) Foreign Application Priority Data

May 15, 2023 (JP) ................................ 2023-079776

(51) Int. Cl.

| | |
|---|---|
| ***A61B 6/42*** | (2024.01) |
| ***A61B 6/00*** | (2006.01) |
| ***G01T 1/175*** | (2006.01) |
| ***G01T 3/00*** | (2006.01) |
| ***H02J 7/34*** | (2006.01) |

(Continued)

(52) U.S. Cl.

CPC .............. *A61B 6/56* (2013.01); *A61B 6/4233* (2013.01); *A61B 6/4405* (2013.01); *A61B 6/487* (2013.01); *G01T 1/175* (2013.01); *G01T 3/006* (2013.01); *H02J 7/342* (2020.01); *H02J 7/345* (2013.01); *H02J 7/82* (2026.01); *H02J 2105/44* (2026.01);

(Continued)

(58) Field of Classification Search

None

See application file for complete search history.

(56) References Cited

U.S. PATENT DOCUMENTS 7,696,484 B2 * 4/2010 Yokoyama ............... A61B 6/00 250/370.09
7,696,722 B2 * 4/2010 Utschig .................. G03B 42/04 320/114

(Continued)

FOREIGN PATENT DOCUMENTS

JP 2012063341 A 3/2012
JP 2012070879 A * 4/2012 ........... A61B 6/4233
JP 2012239657 A * 12/2012

*Primary Examiner* — Thomas R Artman

(74) *Attorney, Agent, or Firm* — Buchanan Ingersoll & Rooney PC

(57) ABSTRACT

A radiographic imaging apparatus includes: a radiographic imager that performs imaging; a built-in power storage device that supplies electric power to the imager, an attachment portion to which an external power storage device that supplies electric power to the imager is to be detachably attached; a connector that is electrically connectable to an external apparatus; and a hardware processor that, in a case where the processor is connected to the external apparatus by the connector and the imager is performing imaging, performs control to supply electric power supplied from the external apparatus to the imager, and in a case where the processor is connected to the external apparatus by the connector and the imager is not performing imaging, performs control to supply the electric power supplied from the external apparatus to the built-in power storage device or the external power storage device attached to the attachment portion.

17 Claims, 7 Drawing Sheets

(51) Int. Cl.
*H02J 7/82* (2026.01)
*H02J 105/44* (2026.01)
*H02J 105/46* (2026.01)

(52) U.S. Cl.
CPC ....... *H02J 2105/46* (2026.01); *H02J 2207/50* (2020.01)

(56) References Cited

U.S. PATENT DOCUMENTS

| | | | | |
|---|---|---|---|---|
| 8,786,257 | B2 * | 7/2014 | Eguchi | A61B 6/563 320/132 |
| 9,425,635 | B2 * | 8/2016 | Mako | H02J 7/0068 |
| 11,540,802 | B2 * | 1/2023 | Kim | A61B 6/5205 |
| 11,950,952 | B2 * | 4/2024 | Kim | A61B 6/467 |
| 2008/0054182 | A1 * | 3/2008 | Yokoyama | G03B 42/04 378/189 |
| 2008/0240358 | A1 * | 10/2008 | Utschig | H01M 50/256 378/107 |
| 2009/0232278 | A1 * | 9/2009 | Ohara | A61B 6/00 378/116 |
| 2011/0261928 | A1 * | 10/2011 | Ohta | A61B 6/0478 378/189 |
| 2012/0133339 | A1 * | 5/2012 | Eguchi | A61B 6/56 320/162 |
| 2013/0270913 | A1 * | 10/2013 | Mako | A61B 6/56 307/66 |
| 2021/0137484 | A1 * | 5/2021 | Kim | A61B 6/467 |
| 2023/0104097 | A1 * | 4/2023 | Kim | A61B 6/56 378/198 |
| 2024/0385341 | A1 * | 11/2024 | Takamiya | H02J 7/342 |

* cited by examiner

RADIOGRAPHIC IMAGING APPARATUS AND RADIOGRAPHIC IMAGING SYSTEM

BACKGROUND OF THE INVENTION

Technical Field

The present invention relates to a radiographic imaging apparatus and a radiographic imaging system.

Description of Related Art

There is known a radiographic imaging apparatus (flat panel detector (FPD)) that captures a radiographic image (radiograph) by detecting, with radiation detection elements, radiation emitted from a radiation source and passing through a subject. A conventional radiographic imaging apparatus is integrated with an imaging stand or the like, but in recent years, a portable radiographic imaging apparatus with radiation detection elements or the like housed in a housing has been developed and put into practical use.

A portable radiographic imaging apparatus, which generally includes a built-in power storage device such as a built-in battery, becomes unable to perform imaging when the remaining charge amount of the built-in power storage device runs out. Further, in recent years, development of a portable radiographic imaging apparatus capable of moving image shooting has been advanced, but since power consumption of moving image shooting is larger than that of still image shooting, the remaining charge amount tends to run out.

Then, for example, in Japanese Unexamined Patent Publication No. 2012-63341, there is disclosed a radiographic image detection device having two battery attachment portions to which battery units can be attached to be able to operate by attaching and replacing detachable batteries. In this radiographic image detection device, a power supply path is switched in accordance with the attachment states and conditions of the remaining charge amounts of the batteries.

SUMMARY OF THE INVENTION

However, the radiographic image detection device of Japanese Unexamined Patent Publication No. 2012-63341 is configured to use two detachable battery units while appropriately replacing batteries, and it is impossible to supply power to an FPD from an external apparatus capable of supplying power, such as a cradle or a medical cart. Therefore, there are problems that battery management is complicated, it takes time and effort to replace batteries, consumption of batteries are severe, batteries tend to run out, and the like.

The present invention has been made in view of the above problems, and objects of the present invention include optimizing a power supply path including power supply from an external apparatus in a radiographic imaging apparatus, and suppressing time and effort for replacement of a power storage device(s), consumption of the power storage device, and running out of the remaining charge amount thereof.

To achieve at least one of the abovementioned objects, according to an aspect of the present invention, a radiographic imaging apparatus reflecting one aspect of the present invention includes:

- a radiographic imager that performs imaging, thereby capturing a radiographic image;
- a built-in power storage device that supplies electric power to the radiographic imager;
- an attachment portion to which an external power storage device that supplies electric power to the radiographic imager is to be detachably attached;
- a connector that is electrically connectable to an external apparatus; and
- a hardware processor that, in a case where the hardware processor is connected to the external apparatus by the connector and the radiographic imager is performing imaging, performs control to supply electric power supplied from the external apparatus to the radiographic imager, and in a case where the hardware processor is connected to the external apparatus by the connector and the radiographic imager is not performing imaging, performs control to supply the electric power supplied from the external apparatus to the built-in power storage device or the external power storage device attached to the attachment portion.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein.

DETAILED DESCRIPTION

Hereinafter, one or more embodiments of the present invention will be described with reference to the drawings.

However, the embodiments described below have various limitations which are technically preferable for carrying out the present invention. Therefore, the technical scope of the present invention is not limited to the following embodiments and illustrated examples.

(Configuration of Radiographic Imaging System 100)

First, a configuration of a radiographic imaging system 100 according to the present embodiment will be described.

Figure 1:
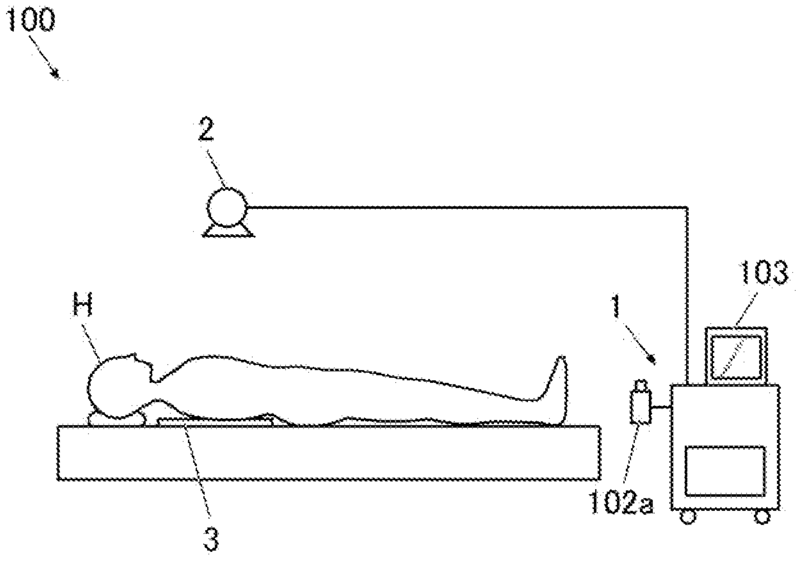
FIG. 1 shows an example of the overall configuration of a radiographic imaging system.

FIG. 1 is a diagram illustrating an example of the entire configuration of a radiographic imaging system 100 in the present embodiment. As shown in FIG. 1, the radiographic imaging system 100 includes a console 1, a radiation source 2, and a flat panel detector (FPD) cassette 3 (radiographic imaging apparatus). Note that FIG. 1 illustrates an example in which the console 1 is integrated with a movable medical cart, but the present invention is not limited thereto.

The console 1 receives an operation such as selection of an imaging menu 130*a* (refer to FIGS. 10 and 11) by a user, and controls imaging in the radiographic imaging system 100 based on the user operation. Furthermore, the console 1 acquires information indicating the states of the radiation source 2 and the FPD cassette 3 and displays the information on a display part 103.

Figure 2:
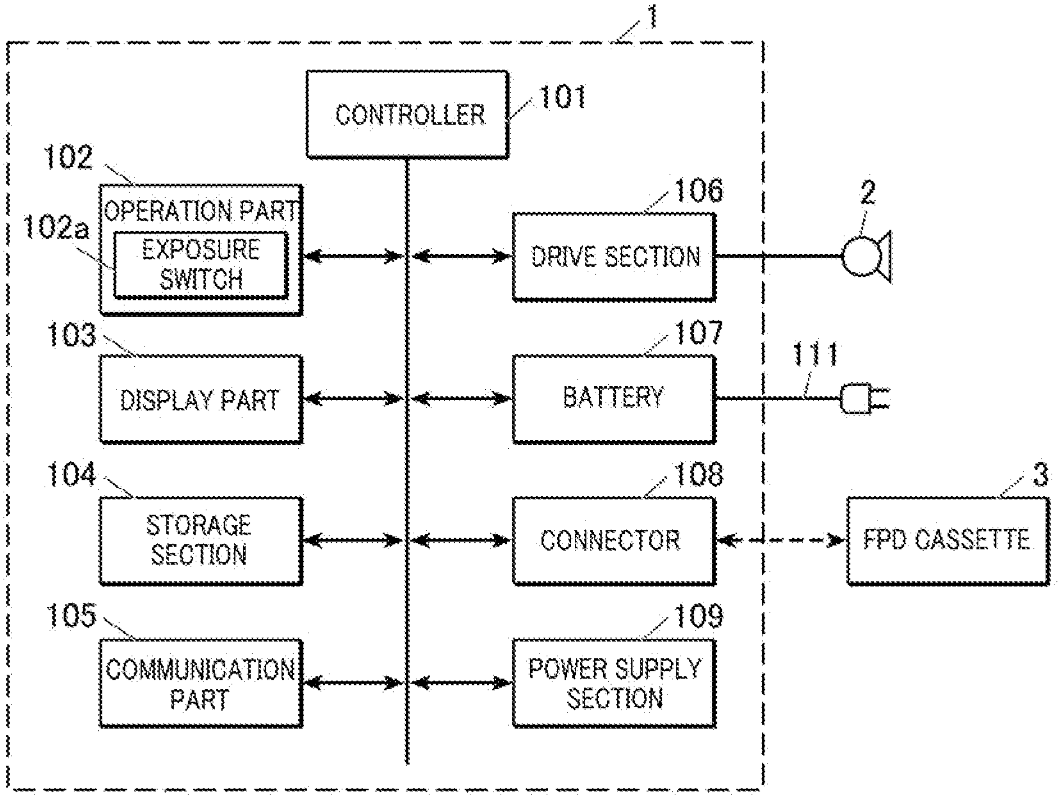
FIG. 2 is a block diagram illustrating a functional configuration of a console.

FIG. 2 is a block diagram illustrating the functional configuration of the console 1. As illustrated in FIG. 2, the console 1 includes a controller 101, an operation part 102, a display part 103 (display), a storage section 104, a communication part 105, a drive section 106, a battery 107, a connector 108, and a power supply section 109.

The controller 101 includes a central processing unit (CPU), a random access memory (RAM), and the like. In response to an input from the operation part 102, the CPU of the controller 101 reads a system program and various process programs stored in the storage section 104, expands the programs in the RAM, and executes various processes in accordance with the expanded programs.

The operation part 102 includes a touch screen or the like in which transparent electrodes are arranged in a lattice shape so as to cover the surface of the display part 103. The operation part 102 detects a position pressed with a finger, a touch pen, or the like, and inputs the position information as operation information to the controller 101.

The operation part 102 further includes an exposure switch 102*a* with which the user provides an instruction to start radiation exposure.

The display part 103 includes a monitor such as a liquid crystal display (LCD) and a cathode ray tube (CRT). The display part 103 performs display in accordance with an instruction of a display signal input from the controller 101.

The storage section 104 is formed by a nonvolatile semiconductor memory, a hard disk, or the like. The storage section 104 stores various programs executed by the controller 101, parameters necessary for execution of processes by the programs, data such as processing results and so forth.

The storage section 104 also stores examination order information received from a radiology information system (RIS) (not illustrated) or the like, captured radiographic images, and the like.

The communication part 105 transmits and receives data to and from external apparatuses such as the FPD cassette 3 by wired communication or wireless communication.

The drive section 106 is a circuit that drives the tube of the radiation source 2. The drive section 106 and the radiation source 2 are connected to each other via a cable.

The battery 107 supplies electric power to the components of the console 1 and the radiation source 2. The battery 107 can be charged from the outside via an AC cable 111.

The connector 108 is electrically connected to a connector 308 of the FPD cassette 3 via, for example, a cable or the like.

The power supply section 109 supplies electric power to the FPD cassette 3 connected via the connector 108 by electric power supplied from the battery 107 based on the control from the controller 101.

The radiation source 2 is driven by the drive section 106 to irradiate a subject H with radiation (X-rays).

The FPD cassette 3 is a portable radiographic imaging apparatus that is compatible with still image shooting and moving image shooting. The still image shooting refers to acquiring one image of a subject in response to one imaging operation (pressing of the exposure switch 102*a*). Moving image shooting refers to acquiring a plurality of images of a subject by irradiating the subject with radiation such as X-rays in a pulsed manner (pulsed irradiation) or a continuous manner (continuous irradiation) in response to one imaging operation. Pulsed irradiation refers to repeatedly emitting radiation in a pulsed manner at predetermined time intervals. Continuous irradiation refers to continuously emitting radiation at a low dose rate without interruption.

As illustrated in FIG. 1, the FPD cassette 3 is arranged at a position facing the radiation source 2 with the subject H interposed therebetween. The FPD cassette 3 generates charges corresponding to the radiation that has been emitted from the radiation source 2 and has passed through the subject H, and reads the generated charges as image data.

Figure 3A:
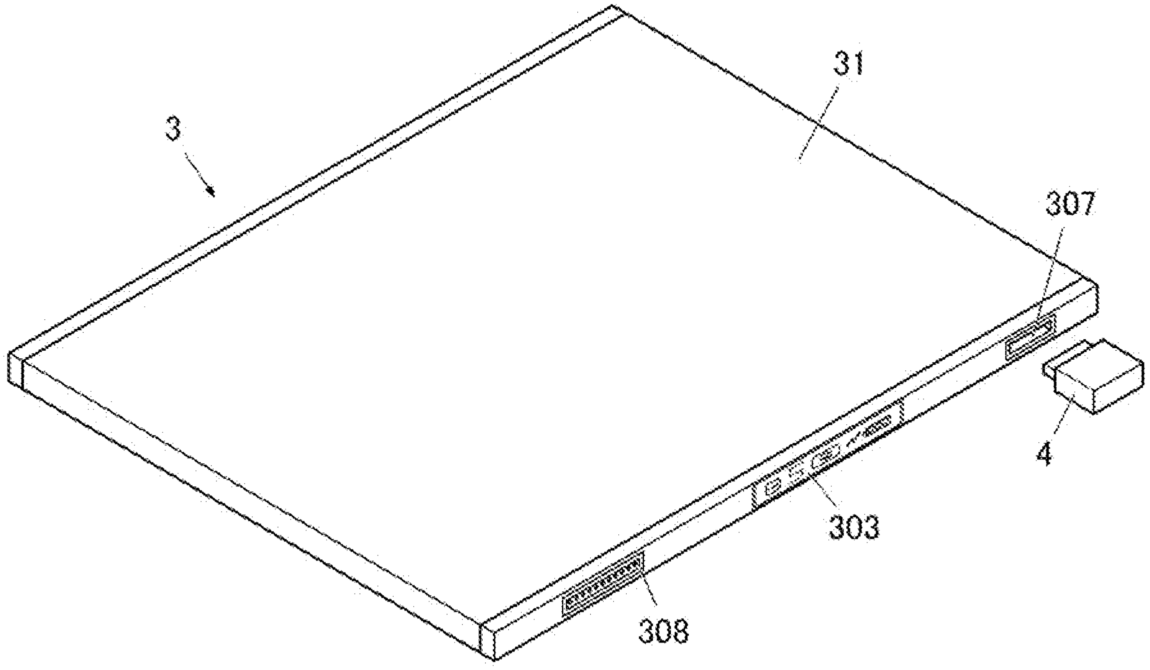
FIG. 3A is a perspective view illustrating the external appearance of an FPD cassette.
Figure 4:
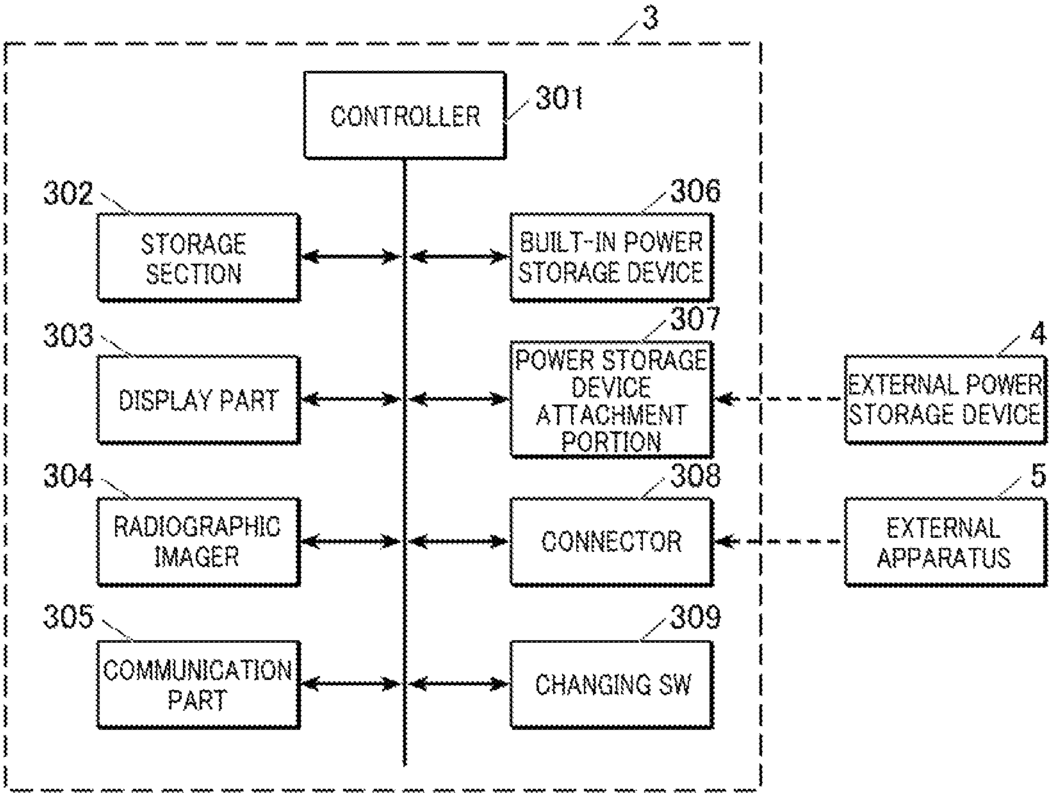
FIG. 4 is a block diagram illustrating a functional configuration of the FPD cassette.

FIG. 3A is a perspective view illustrating the external appearance configuration of the FPD cassette 3. FIG. 4 is a block diagram illustrating a functional configuration of the FPD cassette 3.

As illustrated in FIGS. 3A and 4, the FPD cassette 3 is configured to include a controller 301 (hardware processor), a storage section 302, a display part 303 (display), a radiographic imager 304, a communication part 305, a built-in power storage device 306, a power storage device attachment portion 307, a connector 308, a changing SW 309, and the like.

The controller 301 includes a central processing unit (CPU), a random access memory (RAM), and the like. The CPU of the controller 301 reads various programs stored in the storage section 302, expands the programs in the RAM, and centrally controls each unit of the FPD cassette 3 in accordance with the expanded programs.

The storage section 302 is composed of a nonvolatile semiconductor memory and the like. The storage section 302 stores various programs executed by the controller 301, parameters necessary for execution of processes by the programs, data such as processing results and so forth.

The storage section 302 also temporarily stores captured radiographic images.

The display part 303 displays various information under the control of the controller 301. The display part 303 is, for example, as illustrated in FIG. 3A, provided on the side surface of a housing 31 of the FPD cassette 3.

The radiographic imager 304 includes, for example, radiation detection elements two dimensionally arranged on a glass substrate. The radiation detection elements are formed by semiconductor image sensors, such as photodiodes. Each radiation detection element detects radiation emitted from the radiation source 2 and passing through at least the subject H, in accordance with the intensity of the radiation, converts the detected radiation into an electric signal, and accumulates the electric signal. For example, a switching unit such as a thin film transistor (TFT) is connected to each radiation detection element. The switching unit controls accumulation and readout of electric signals in the radiation detection element to acquire image data. Note that FPDs are classified into an indirect conversion type in which radiation is converted into electrical signals by photoelectric conversion elements via a scintillator and a direct conversion type in which radiation is directly converted into electrical signals, and any of these types may be used.

The communication part 305 transmits and receives data to and from the console 1 and the like in a wireless manner or a wired manner via an antenna (not shown) or the connector 308.

The built-in power storage device 306 stores electric power supplied via the changing SW 309 (is charged), and supplies the power to each unit including the radiographic imager 304. As the built-in power storage device 306, for example, a lead storage battery, an Ni—Cd storage battery, an Ni-MI battery, an LIB (lithium-ion battery), an Li—Po secondary battery, an Na-ion battery, an electric double-layer capacitor, a lithium-ion capacitor (LIC), or the like can be used. Among them, an LIC is capable of rapid charge and discharge, has high durability and safety, and is lightweight. Therefore, an LIC is preferably used as the built-in power storage device 306. In the present embodiment, the description will be given assuming that the built-in power storage device 306 is an LIC.

Figure 3B:
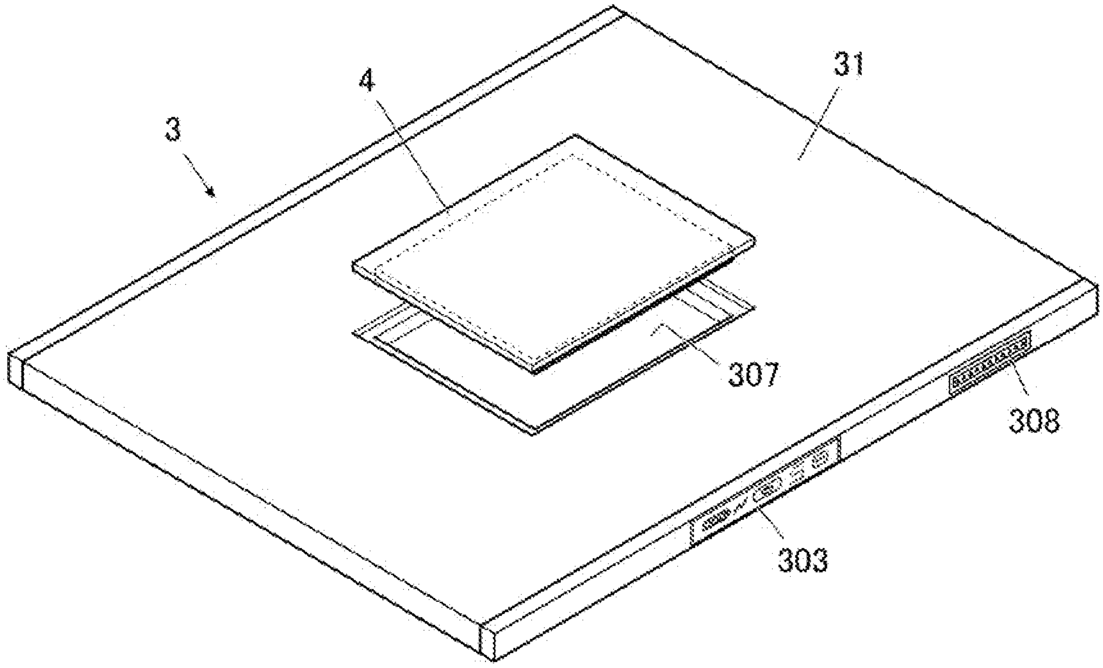
FIG. 3B shows an FPD cassette provided with a power storage device attachment portion on the back surface of a housing.

The power storage device attachment portion 307 is configured such that the external power storage device 4 can be attached thereto and detached therefrom, and electrically connects the attached external power storage device 4. The power storage device attachment portion 307 is, for example, as illustrated in FIG. 3A, provided on the side surface of the housing 31 of the FPD cassette 3. Alternatively, as illustrated in FIG. 3B, the power storage device attachment portion 307 may be configured to include, on the back surface of the housing 31 of the FPD cassette 3, a recess in which a plate-shaped external power storage device 4 can be stored. With such a configuration, when the external power storage device 4 is attached to the power storage device attachment portion 307, the back surface of the housing 31 can be substantially flat. In addition, it is possible to prevent an increase in the total capacity of the FPD cassette 3 due to the attachment of the external power storage device 4 to the FPD cassette 3. Note that the power storage device attachment portion 307 may be provided on both the side surface and the back surface of the housing 31.

The power storage device attachment portion 307 includes a detector (not illustrated) that detects whether the external power storage device 4 is attached. As the detector, for example, a photosensor, a microswitch, or the like can be used.

Note that the power storage device attachment portion 307 may include a lock mechanism for fixing the attached external power storage device 4. As a result, it is possible to prevent the external power storage device 4 from being detached during imaging. The power storage device attachment portion 307 may have a waterproof mechanism. As a result, it is possible to prevent liquid from entering from the power storage device attachment portion 307 during use or sterilization of the FPD cassette 3.

Furthermore, an extension device having a function other than power storage and power supply may be attachable to the power storage device attachment portion 307. For example, when nothing is attached to the power storage device attachment portion 307, dust such as hair may be caught in a recess of the power storage device attachment portion 307. Therefore, for a user who does not use the external power storage device 4 with emphasis on lightweight, for example, a dummy power storage device that includes only a housing and no content may be attachable as an extension device. Alternatively, as the expansion device, a small display for displaying information of the FPD cassette 3 may be attached to the power storage device attachment portion 307.

The external power storage device 4 attached to the power storage device attachment portion 307 stores electric power supplied (is charged) via the changing SW 309, and supplies the power to each unit including the radiographic imager 304. As the external power storage device 4, a lead storage battery, an Ni—Cd storage battery, an Ni-MI battery, an LIB, an Li—Po secondary battery, an Na-ion battery, an electric double-layer capacitor, an LIC, or the like can be used. In particular, an LIB has a larger capacity than other storage batteries. Therefore, an LIB is preferably used as the external power storage device 4. In the description of the present embodiment, the external power storage device 4 is an LIB.

It is preferable that the external power storage device 4 be colored differently from the FPD cassette 3, be coated (surface-treated) differently from the FPD cassette 3, or be provided with a mark serving as a mark. Accordingly, the user can easily recognize visually or tactually whether or not the external power storage device 4 is attached to the FPD cassette 3. Furthermore, colors, coatings, and marks may be provided for the respective types of external power storage devices 4. Thus, the user can easily identify which type of external power storage device 4 is attached to the FPD cassette 3.

The connector 308 is a connecting part that can be electrically connected to an external apparatus 5. The connector 308 is connected to, for example, a connector of the external apparatus 5 directly or via a cable. The external apparatus 5 is, for example, an external apparatus, such as a medical cart, an imaging stand, or a cradle, capable of supplying power to the FPD cassette 3. In the present embodiment, a medical cart is integrally formed with the console 1.

Figure 5:
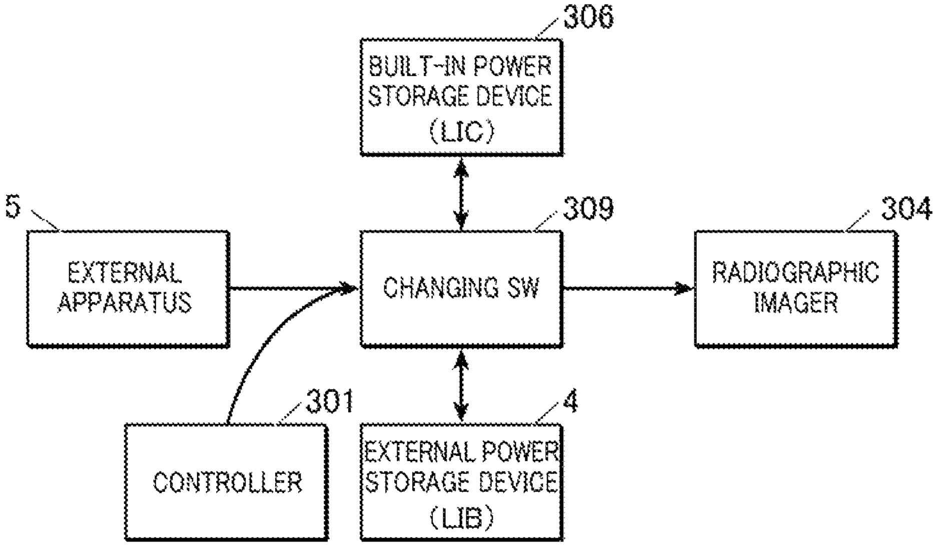
FIG. 5 is a block diagram illustrating a power supply path in the FPD cassette.

The changing switch (SW) 309 changes a power supply path under the control of the controller 301 (see FIG. 5).

(Operation of Radiographic Imaging System 100)

Next, operation of the radiographic imaging system 100 will be described.

In radiographic imaging, for example, a radiographer who is a user causes the display part 103 to display an imaging screen 130 of a patient (subject H) to be imaged in the console 1 (see FIGS. 10 and 11), and selects an imaging menu **130*a* by operating the operation part 102. The imaging menu 130*a* includes, for example, an imaging mode (a still image shooting mode or a moving image shooting mode), an imaging part, and an imaging direction. The moving image shooting mode includes a dynamic image shooting mode for capturing a moving image of the dynamic state of the imaging part of the subject H and a fluoroscopic image shooting mode for capturing a fluoroscopic image of the imaging part of the subject H. The user also positions the subject H, the radiation source 2, and the FPD cassette 3**.

In the console 1, when an imaging menu **130*a* is selected by an operation on the operation part 102, the controller 101 sets radiation emission conditions at the selected imaging menu 130*a* in the drive section 106. Further, the controller 101 transmits image reading conditions corresponding to the selected imaging menu 130*a* to the FPD cassette 3 via the communication part 105**.

When preparations for imaging are completed, the user presses a first switch of the exposure switch **102*a*** and then presses a second switch thereof.

When the first switch of the exposure switch 102*a* is pressed, the controller 101 causes the drive section 106 to start rotation of the positive electrode of the X-ray tube of the radiation source 2, thereby bringing the radiation source 2 into a standby state. The controller 101 transmits a depression notification signal of the first switch to the FPD cassette 3 via the communication part 105. When the controller 301 of the FPD cassette 3 receives the depression notification signal of the first switch via the communication part 305, the controller 301 starts a reset process for removing charges remaining in the radiation detection elements from the inside of the radiation detection elements in the radiographic imager 304. When the reset process ends, the controller 301 notifies the console 1 of the completion of the reset process via the communication part 305.

When the second switch of the exposure switch 102*a* is pressed and the completion notification of the reset process is received, the controller 101 causes the drive section 106 to drive the radiation source 2 to emit radiation beams on the basis of the set radiation emission conditions. Upon performing notification of the completion of the reset process, the controller 301 of the FPD cassette 3 causes the radiographic imager 304 to accumulate radiation and read an image based on the received image reading conditions, and captures a radiographic image (main image). After capturing a series of radiographic images, the controller 301 causes the radiographic imager 304 to accumulate and read charges in the radiation detection elements in a state in which no radiation is emitted, and captures an image (dark image). Next, the controller 301 performs various kinds of correction, such as offset correction using the dark image, on the radiographic image, and transmits the corrected radiographic image to the console 1 via the communication part 305.

The console 1 performs image processing on the radiographic image received from the FPD cassette 3 and displays the processed radiographic image on the display part 103.

The above is a rough flow of imaging in the radiographic imaging system 100.

As described above, imaging can be performed in the moving image shooting mode in the radiographic imaging system 100. However, the power consumption of moving image shooting is larger than that of still image shooting. For this reason, it may occur that the remaining amount (remaining charge amount) of the built-in power storage device 306 or the attached external power storage device 4 runs out in the middle of imaging, and photographing cannot be completed.

Therefore, in the FPD cassette 3, the power supply path including power supply from the external apparatus 5 is optimized so that the time and effort for replacing a power storage device, the consumption of the power storage device, and the shortage of the remaining charge amount can be suppressed.

FIG. 5 is a block diagram illustrating the power supply path in the FPD cassette 3.

As illustrated in FIG. 5, in the FPD cassette 3, the changing SW 309 switches the power supply path under the control of the controller 301. In the present embodiment, the changing SW 309 switches the power supply path such that power supplied from the external apparatus 5 is supplied to the radiographic imager 304, the built-in power storage device 306, or the external power storage device 4 based on the control of the controller 301. Furthermore, under the control of the controller 301, the changing SW 309 performs switching such that the power of the external power storage device 4 is supplied to either the radiographic imager 304 or the built-in power storage device 306. Further, the changing SW 309 performs switching so as to supply the electric power of the built-in power storage device 306 to the radiographic imager 304 based on the control of the controller 301. The switching may be performed such that the power of the built-in power storage device 306 is supplied to the external power storage device 4.

Figure 6:
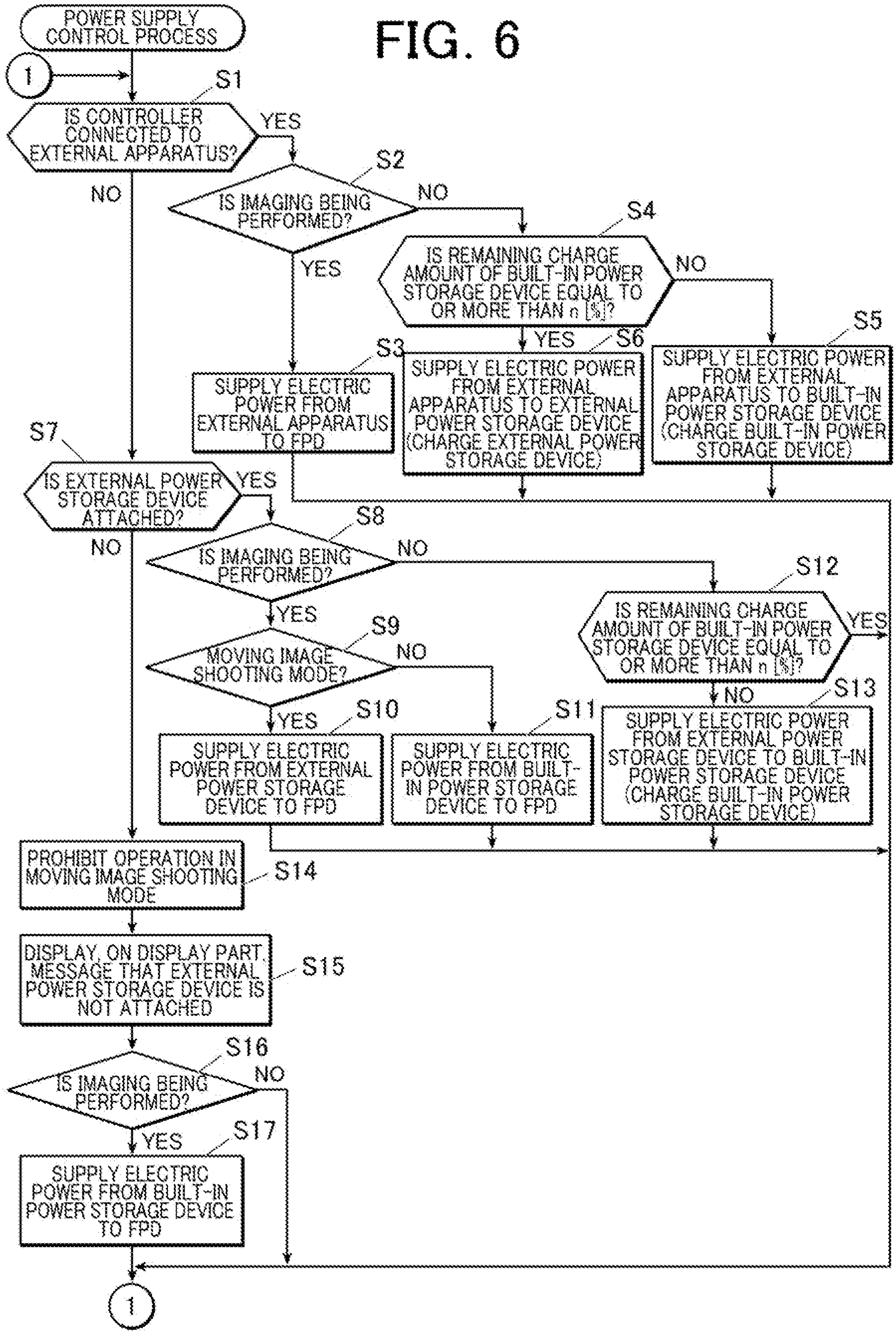
FIG. 6 is a flowchart illustrating the flow of a power supply control process executed by a controller of the FPD cassette.

The controller 301 executes the power supply control process illustrated in FIG. 6 while a power switch (not illustrated) of the FPD cassette 3 is ON. Thus, the controller 301 controls the switching of the power supply path by the changing SW 309 in accordance with the connection state of the external apparatus 5, the attachment state of the external power storage device 4, the imaging state, and the like. The power supply control process illustrated in FIG. 6 is executed by the CPU of the controller 301 in cooperation with a program stored in the storage section 302.

In the power supply control process, first, the controller 301 determines whether the controller 301 is wire-connected to the external apparatus 5 by the connector 308 (Step S1).

The form of wired connection herein includes connection of the FPD cassette 3 and the external apparatus 5 by connecting a cable to which the external apparatus 5 is connected to the connector 308, and direct connection of a connector of the external apparatus 5 to the connector 308.

If the controller 301 determines that the controller 301 is wire-connected to the external apparatus 5 by the connector 308 (Step S1; YES), the controller 301 determines whether the radiographic imager 304 is performing imaging (Step S2).

Here, the term "performing imaging" refers to, for example, during execution of an imaging operation including at least accumulation and readout operations in the radiographic imager 304. In the present embodiment, the controller 301 determines that the radiographic imager 304 is performing imaging, for example, if the radiographic imager 304 is performing one of the operations of storing a main image, reading out a main image, storing a dark image, and reading out a dark image.

If the controller 301 determines that the radiographic imager 304 is performing imaging (Step S2; YES), the controller 301 controls the changing SW 309 such that electric power supplied from the external apparatus 5 is supplied to the radiographic imager 304 (Step S3), and returns to Step S1.

Note that the radiographic imager 304 is abbreviated as FPD in FIG. 6.

If the controller 301 determines that the radiographic imager 304 is not performing imaging (Step S2; NO), the controller 301 determines whether the remaining charge amount (%) of the built-in power storage device 306 is higher than or equal to a predetermined value n ($n \geq 0$) (Step S4). The predetermined value n is a value of the remaining charge amount that can be dealt with at least hot swapping.

When it is determined that the remaining charge amount (%) of the built-in power storage device 306 is not equal to or more than the predetermined value n ($n \geq 0$) (Step S4; NO), the controller 301 controls the changing SW 309 such that electric power supplied from the external apparatus 5 is supplied to the built-in power storage device 306 (Step S5), and returns to Step S1.

When it is determined that the remaining charge amount (%) of the built-in power storage device 306 is equal to or more than the predetermined value n ($n \geq 0$) (Step S4; YES), the controller 301 controls the changing SW 309 so as to supply electric power supplied from the external apparatus 5 to the external power storage device 4 attached to the power storage device attachment portion 307 (Step S6), and returns to Step S1.

That is, when imaging is not being performed, the controller 301 supplies the electric power supplied from the external apparatus 5 to the built-in power storage device 306 preferentially. This is to ensure the remaining charge amount required for hot swapping. When the remaining charge amount (%) of the built-in power storage device 306 is equal to or more than the predetermined value n (n≥0), that is, when the remaining charge amount required for hot swapping is secured, the electric power supplied from the external apparatus 5 is supplied to the external power storage device 4.

In the present embodiment, the predetermined value n is set to the remaining charge amount that can at least cope with hot swapping, but may be set to a value corresponding to an operation that requires the remaining charge amount higher than that for hot swapping. For example, the predetermined value n may be a value at which a predetermined number of still images can be captured or a value at which a moving image for a predetermined time can be captured. The predetermined value n may be a value set by the user.

On the other hand, when it is determined in Step S1 that the controller 301 is not wire-connected to the external apparatus 5 by the connector 308 (Step S1; NO), the controller 301 determines whether the external power storage device 4 is attached to the power storage device attachment portion 307 (Step S7).

For example, the controller 301 determines, based on whether the external power storage device 4 is detected by a detector provided on the power storage device attachment portion 307, whether the external power storage device 4 is attached.

If the controller 301 determines that the external power storage device 4 is attached to the power storage device attachment portion 307 (Step S7; YES), the controller 301 determines whether the radiographic imager 304 is performing imaging (Step S8).

If the controller 301 determines that the radiographic imager 304 is performing imaging (Step S8; YES), the controller 301 determines whether the radiographic imager 304 is operating in the moving image shooting mode (Step S9).

If the controller 301 determines that the radiographic imager 304 is operating in the moving image shooting mode (Step S9; YES), the controller 301 controls the changing SW 309 such that electric power is supplied to the radiographic imager 304 from the external power storage device 4 attached to the power storage device attachment portion 307 (Step S10), and returns to Step S1.

During imaging in the moving image shooting mode in which power consumption is large, power is supplied to the radiographic imager 304 from the external power storage device 4 having a large capacity. Thus, it is possible to prevent the remaining charge amount of the built-in power storage device 306 from running out or the remaining charge amount for hot swapping from not being secured during imaging.

If it is determined that the radiographic imager 304 is not operating in the moving image shooting mode (Step S9; NO), the controller 301 controls the changing SW 309 such that electric power is supplied from the built-in power storage device 306 to the radiographic imager 304 (Step S11), and returns to Step S1.

The built-in power storage device 306 (LIC) has high durability. Therefore, when the mode is not the moving image shooting mode in which power consumption is large, power is supplied from the built-in power storage device 306 to the radiographic imager 304 preferentially. As a result, the charge/discharge cycles of the external power storage device 4 can be reduced, and the life of the external power storage device 4 can be extended.

On the other hand, when determining in Step S8 that the radiographic imager 304 is not performing imaging (Step S8: NO), the controller 301 determines whether the remaining charge amount (%) of the built-in power storage device 306 is equal to or higher than the predetermined value n(n≥0) (Step S12).

If the controller 301 determines that the remaining charging amount (%) of the built-in power storage device 306 is not equal to or more than the predetermined value n(n≥0) (Step S12; NO), the controller 301 controls the changing SW 309 such that electric power is supplied to the built-in power storage device 306 from the external power storage device 4 attached to the power storage device attachment portion 307 (Step S13), and returns to Step S1.

As a result, the remaining charge amount of the built-in power storage device 306 can be secured.

If the controller 301 determines that the remaining charge amount (%) of the built-in power storage device 306 is higher than or equal to the predetermined value n(n≥0) (Step S12; YES), the controller 301 returns to Step S1.

On the other hand, if the controller 301 determines in Step S7 that the external power storage device 4 is not attached to the power storage device attachment portion 307 (Step S7; NO), the controller 301 prohibits the radiographic imager 304 from operating in the moving image shooting mode (Step S14). That is, when determining that the external power storage device 4 is not attached to the power storage device attachment portion 307, the controller 301 prohibits moving image shooting. Furthermore, the controller 301 causes the display part 303 to display an indication indicating that the external power storage device 4 is not attached (Step S15).

Next, the controller 301 determines whether the radiographic imager 304 is performing imaging (Step S16).

If it is determined that imaging is being performed (Step S16; YES), the controller 301 controls the changing SW 309 such that electric power is supplied from the built-in power storage device 306 to the radiographic imager 304 (Step S11), and returns to Step S1.

If it is determined that imaging is not being performed (Step S16; NO), the controller 301 returns to Step S1.

The controller 301 repeatedly executes the power supply control process while the power switch of the FPD cassette 3 is ON.

In this way, the controller 301 optimizes the power supply path according to the connection state of the external apparatus, the attachment state of the external power storage device 4, the imaging state, and the like by executing the power supply control process while the power switch is ON. Therefore, it is possible to suppress the time and effort for replacing a power storage device, the consumption of the power storage device, and the shortage of the remaining charge amount.

Figure 7:
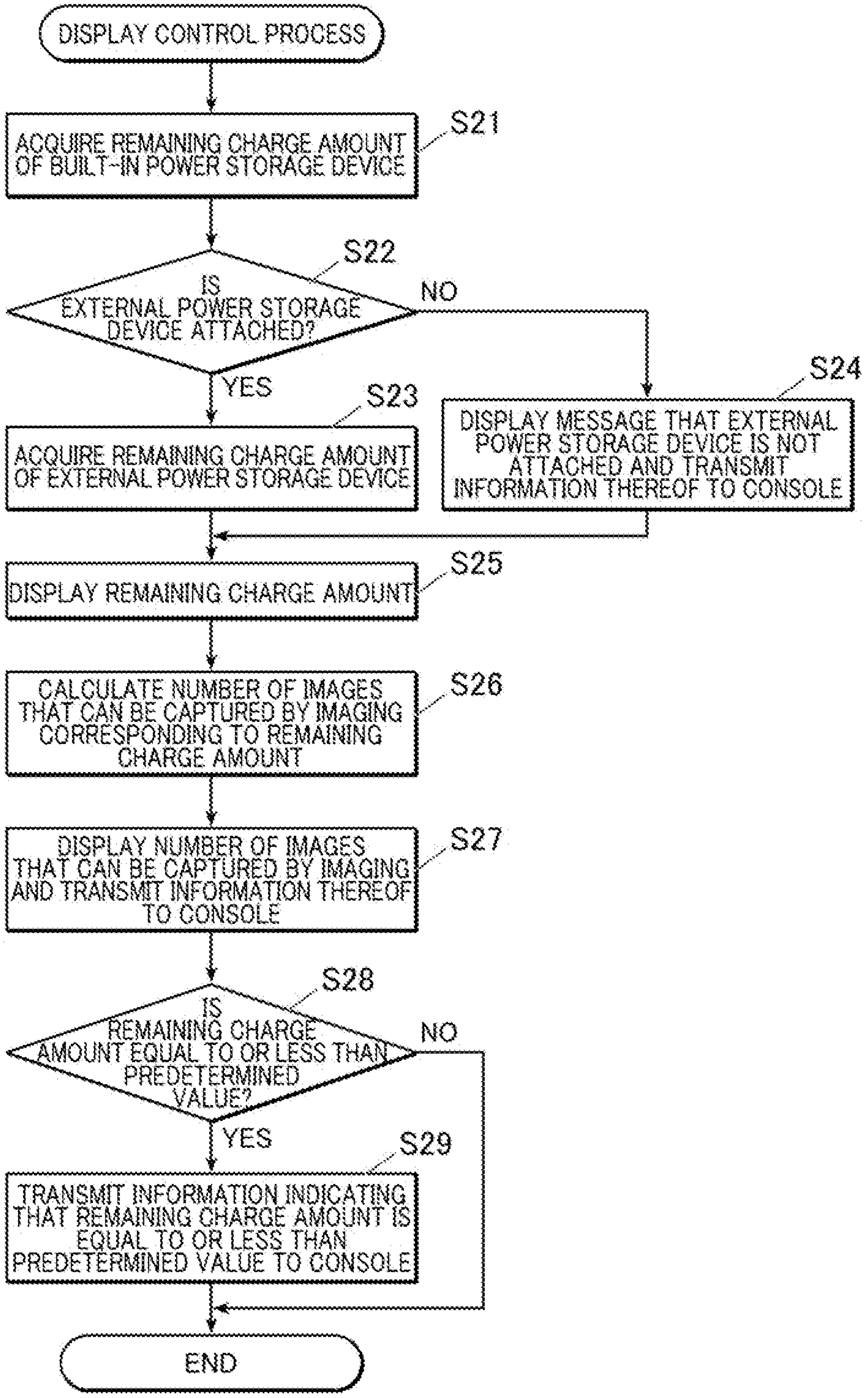
FIG. 7 is a flowchart illustrating the flow of a display control process executed by the controller of the FPD cassette.

In addition, the controller 301 executes the display control process shown in FIG. 7 at every predetermined time, and notifies the user of the remaining charge amounts of the built-in power storage device 306 and the external power storage device 4, the number of images that can be captured by imaging and/or a time period for which imaging can be performed, the fact that the external power storage device 4 is not attached, and the like. The display control process illustrated in FIG. 7 is executed by the CPU of the controller 301 in cooperation with a program stored in the storage section 302.

In the display control process, first, the controller 301 acquires the remaining charge amount of the built-in power storage device 306 (Step S21).

Next, the controller 301 determines whether the external power storage device 4 is attached to the power storage device attachment portion 307 (Step S22).

If the controller 301 determines that the external power storage device 4 is attached to the power storage device attachment portion 307 (Step S22; YES), the controller 301 acquires the remaining charge amount of the external power storage device 4 (Step S23) and proceeds to Step S25.

If the controller 301 determines that the external power storage device 4 is not attached to the power storage device attachment portion 307 (Step S22; NO), the controller 301 causes the display part 303 to display an indication indicating that the external power storage device 4 is not attached. In addition, the controller 301 transmits, to the console 1 via the communication part 305, information indicating that the external power storage device 4 is not attached (Step S24), and proceeds to Step S25.

When the communication part 105 receives from the FPD cassette 3 the information indicating that the external power storage device 4 is not attached, the controller 101 of the console 1 causes the display part 103 to display the information indicating that the external power storage device 4 is not attached to the FPD cassette 3. Thus, it is possible to notify the user that the external power storage device 4 is not attached to the FPD cassette 3.

In Step S25, the controller 301 causes the display part 303 to display an indication(s) indicating the remaining charge amounts of the built-in power storage device 306 and the external power storage device 4 (Step S25).

When the external power storage device 4 is not attached, the controller 301 causes the display part 303 to display only the remaining charge amount of the built-in power storage device 306.

The controller 301 may transmit information indicating the remaining charge amounts of the built-in power storage device 306 and the external power storage device 4 to the console 1 via the communication part 305. Then, when the controller 101 of the console 1 receives the information indicating the remaining charge amounts of the built-in power storage device 306 and the external power storage device 4 from the FPD cassette 3 via the communication part 105, the controller 101 may cause the display part 103 to display the information indicating the remaining charge amounts of the built-in power storage device 306 and the external power storage device 4. As a result, the user can grasp the remaining charge amount(s) in the FPD cassette 3 from the display of the console 1.

Next, the controller 301 calculates the number of images that can be captured by imaging based on the remaining charge amounts of the built-in power storage device 306 and the external power storage device 4 (Step S26).

Next, the controller 301 causes the display part 303 to display the calculated number of images that can be captured by imaging (Step S27). In addition, the controller 301 transmits the number of images that can be captured by imaging to the console 1 via the communication part 305 (Step S27).

The controller 301 may calculate a time period for which imaging can be performed in addition to the number of images that can be captured by imaging, and cause the display part 303 to display the number of images that can be captured by imaging and the time period for which imaging can be performed and/or transmit them to the console 1. The controller 301 may calculate only the time period for which imaging can be performed, and cause the display part 303 to display the time period and/or transmit it to the console 1.

Upon receiving the number of images that can be captured by imaging and/or the time period for which imaging can be performed from the FPD cassette 3 via the communication part 105, the controller 101 of the console 1 causes the display part 103 to display the number of images and/or the time period. Thus, the user can grasp the number of images that can be captured by imaging and/or the time period for which imaging can be performed from the display of the console 1.

Next, the controller 301 determines whether the remaining charge amount of the built-in power storage device 306 and the external power storage device 4 is equal to or less than a predetermined value (Step S28).

For example, the controller 301 determines whether the remaining charge amount of the built-in power storage device 306 and the external power storage device 4 is equal to or less than a predetermined value m(m>0). Examples of the remaining charge amount of the built-in power storage device 306 and the external power storage device 4 include the remaining charge amount obtained by summing the remaining charge amount of the built-in power storage device 306 and the remaining charge amount of the external power storage device 4. The predetermined value m is, for example, a value set in advance on the basis of the remaining charge amount necessary for imaging.

If the controller 301 determines that the remaining charge amount of the built-in power storage device 306 and the external power storage device 4 is not equal to or less than the predetermined value m (Step S28; NO), the controller 301 ends the display control process.

If the controller 301 determines that the remaining charge amount of the built-in power storage device 306 and the external power storage device 4 is equal to or less than the predetermined value m (Step S28; YES), the controller 301 causes the communication part 305 to transmit information indicating that the remaining charge amount of the built-in power storage device 306 and the external power storage device 4 is equal to or less than the predetermined value m to the console 1 (Step S29) and ends the display control process. The controller 301 may display, on the display part 303, information indicating that the remaining charge amount of the built-in power storage device 306 and the external power storage device 4 is equal to or less than the predetermined value m.

When the controller 101 of the console 1 receives, from the FPD cassette 3 via the communication part 105, the information indicating that the remaining charge amount is equal to or less than the predetermined value, the controller 101 causes the display part 103 to display that the remaining charge amount in the FPD cassette 3 is decreasing. Thus, the user can grasp, from the display of the console 1, that the remaining charge amount of the FPD cassette 3 is decreasing.

Figure 8A:
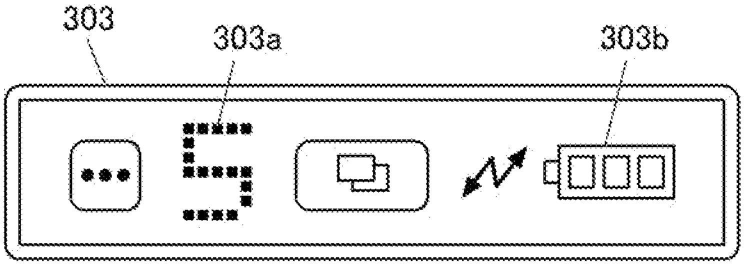
FIG. 8A shows a display example of the number of images that can be captured by imaging and the remaining charge amount in a case where the external power storage device is attached to the FPD cassette.
Figure 8B:
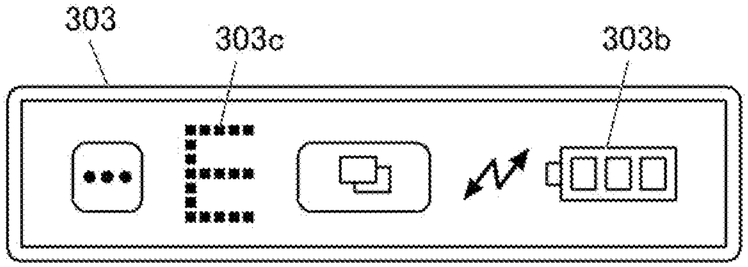
FIG. 8B shows a display example of an error mark in a case where the external power storage device is not attached to the FPD cassette.

FIGS. 8A and 8B show display examples of the display part 303 in the display control process.

In a case where the external power storage device 4 is attached, for example, as illustrated in FIG. 8A, a photographable number 303*a* (the number of images that can be captured by imaging) and a remaining amount indication 303*b* are displayed on the display part 303. In a case where the external power storage device 4 is not attached, for example, as shown in FIG. 8B, an error mark 303*c* and the remaining amount indication 303*b* are displayed on the display part 303. The error mark 303*c* is a mark indicating that the external power storage device 4 is not attached.

Figure 9:
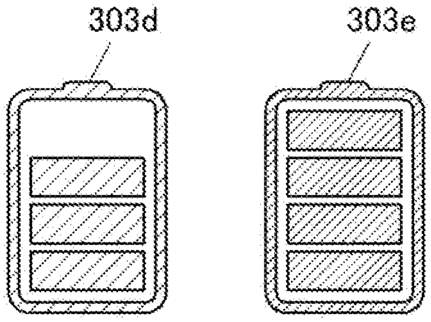
FIG. 9 shows examples of remaining charge amount indications of the FPD cassette.

Note that as illustrated in FIGS. 8A and 8B, as the remaining amount indication, for example, the remaining charge amounts of the built-in power storage device 306 and the external power storage device 4 may be added up to display one remaining amount indication 303*b*. Alternatively, as shown in FIG. 9, a remaining amount indication 303*d* of the built-in power storage device 306 and a remaining amount indication 303*e* of the external power storage device 4 may be displayed separately. In this case, the color of the remaining amount indication may be changed depending on the power storage device.

As described above, the display part 303 of the housing 31 of the FPD cassette 3 displays the photographable number 303*a*, the remaining amount indication 303*b* (303*d*, 303*e*), the error mark 303*c* indicating that the external power storage device 4 is not attached, and the like. Therefore, the user can grasp the remaining charge amount of the FPD cassette 3 and the number of images that can be captured¥ by imaging. Further, when the external power storage device 4 is not attached, the user can recognize that the external power storage device 4 is not attached.

Figure 10:
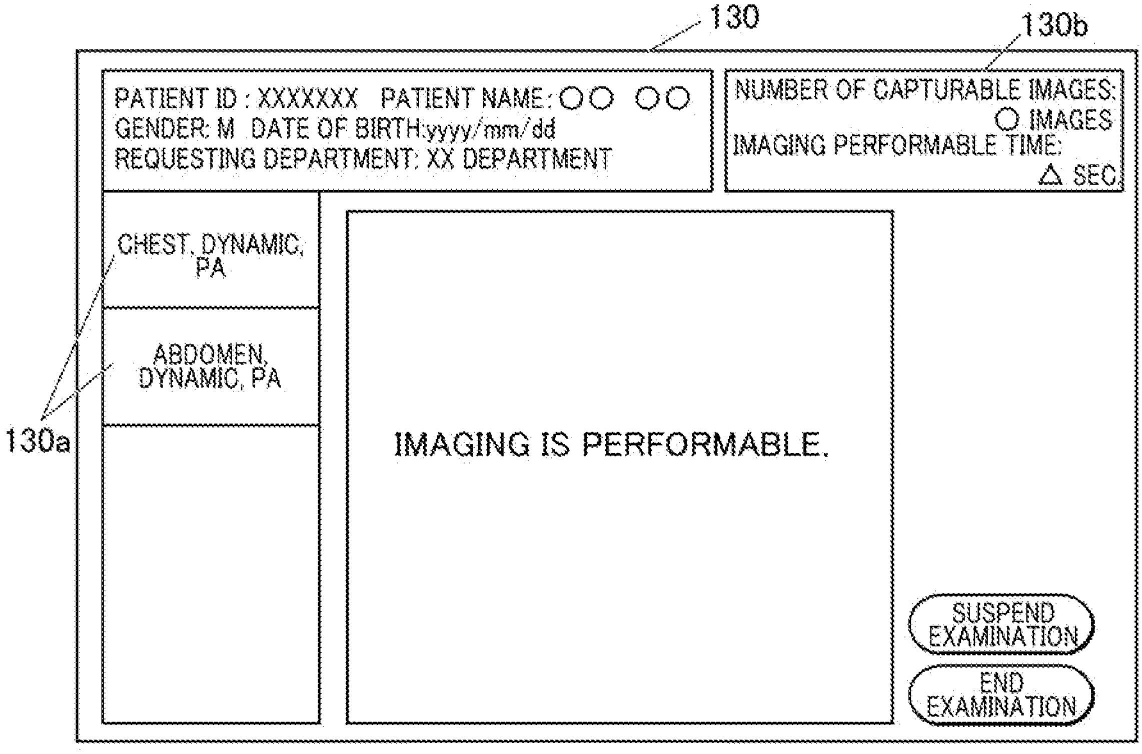
FIG. 10 shows a display example of the number of images that can be captured by imaging and a time period for which imaging can be performed of the FPD cassette, in the console.

FIG. 10 shows a display example on the console 1 in a case where the number of images that can be captured by imaging and the time period for which imaging can be performed are transmitted from the FPD cassette 3 to the console 1 in the display control process.

As shown in FIG. 10, for example, an indication 130*b* indicating the number of images that can be captured by imaging and the time period for which imaging can be performed in the FPD cassette 3 is displayed on the imaging screen 130 displayed by the display part 103 of the console 1. Therefore, the user can grasp the number of images that can be captured by imaging and the time period for which imaging can be performed in the FPD cassette 3 from the display of the console 1.

Figure 11:
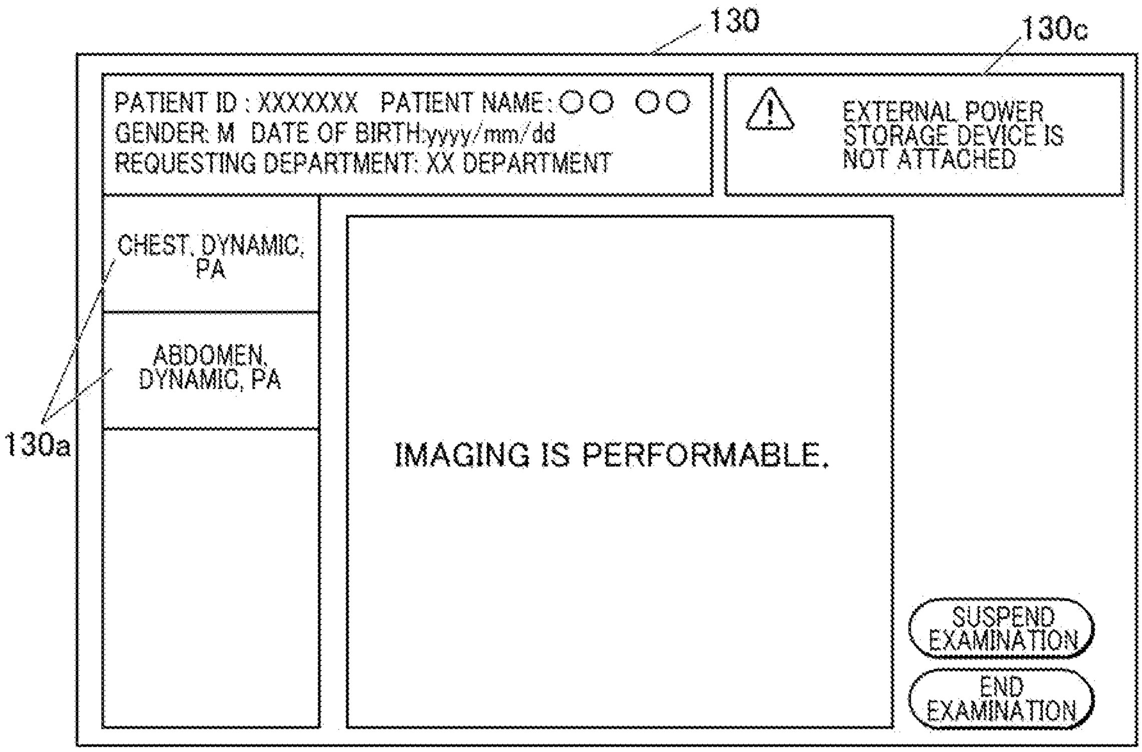
FIG. 11 shows a display example of a message indicating that the external power storage device is not attached to the FPD cassette, in the console.

FIG. 11 shows a display example on the console 1 in a case where information indicating that the external power storage device 4 is not attached is transmitted from the FPD cassette 3 to the console 1 in the display control process.

As illustrated in FIG. 11, for example, a message 130*c* indicating that the external power storage device 4 is not attached to the FPD cassette 3 is displayed on the imaging screen 130 displayed by the display part 103 of the console 1. Therefore, the user can grasp, from the display of the console 1, that the external power storage device 4 is not attached to the FPD cassette 3.

In the console 1, when the information indicating that the external power storage device 4 is not attached is transmitted from the FPD cassette 3, the controller 101 may prohibit the user from making a selection operation of the moving image shooting mode in which the power consumption is large. Examples of a method of prohibiting the selection operation of the moving image shooting mode include a method of performing gray-out of an option related to the moving image shooting mode in the imaging menu 130*a*, and a method of not displaying the moving image shooting mode in options in the imaging menu 130*a*. Thus, it is possible to prevent the user from erroneously selecting the moving image shooting mode.

As described above, the FPD cassette 3 includes the radiographic imager 304, the built-in power storage device 306, the power storage device attachment portion 307 to which the external power storage device 4 is detachably attached, the connector 308 electrically connectable to the external apparatus 5, and the controller 301. In a case where the controller 301 is connected to the external apparatus 5 by the connector 308 and the radiographic imager 304 is performing imaging, the controller 101 performs control such that electric power supplied from the external apparatus 5 is supplied to the radiographic imaging capturing section 304. In a case where the controller 301 is connected to the external apparatus 5 by the connector 308 and the radiographic imager 304 is not performing imaging, the controller 101 performs control such that electric power supplied from the external apparatus 5 is supplied to the built-in power storage device 306 or the external power storage device 4 attached to the power storage device attachment portion 307.

Therefore, in a case where the external apparatus 5 is connected, electric power supplied from the external apparatus 5 is supplied to the radiographic imager 304 during imaging, so that power consumption of the built-in power storage device 306 and the external power storage device 4 can be suppressed. As a result, time and effort for replacing the external power storage device 4, consumption of the built-in power storage device 306 and the external power storage device 4, and running out of the remaining charge amount(s) thereof can be suppressed.

Furthermore, in a case where the controller 301 is connected to the external apparatus 5 by the connector 308 and the radiographic imager 304 is not performing imaging, the controller 301 performs control such that electric power supplied from the external apparatus 5 is preferentially supplied to the built-in power storage device 306. If the remaining charge amount of the built-in power storage device 306 is equal to or greater than a predetermined value, the controller 301 performs control such that electric power supplied from the external apparatus 5 is supplied to the external power storage device 4. Therefore, it is possible to secure the remaining charge amount of the built-in power storage device 306 to be equal to or more than the predetermined value for hot swapping.

Furthermore, for example, use of a lithium-ion capacitor as the built-in power storage device 306 enables rapid charge and discharge, so that even if the remaining charge amount becomes insufficient, the required remaining charge amount can be immediately ensured by charging. In addition, it is possible to realize the built-in power storage device 306 that has high durability and safety and is lightweight. Furthermore, for example, use of a large-capacity lithium-ion battery as the external power storage device 4 makes it possible to cope with the moving image shooting mode that consumes a large amount of power.

Furthermore, in a case where the controller 301 is not connected to the external apparatus 5 by the connector 308, the controller 301 performs control such that electric power is supplied to the radiographic imager 304 from the built-in power storage device 306 or the external power storage device 4 attached to the power storage device attachment portion 307. Therefore, when there is no power supply from the external apparatus 5, power can be supplied to the radiographic imager 304 by the built-in power storage device 306 or the external power storage device 4.

Further, in a case where the controller 301 is not connected to the external apparatus 5 by the connector 308 and the external power storage device 4 is attached to the power storage device attachment portion 307, the controller 301 performs control such that electric power is supplied from the built-in power storage device 306 to the radiographic imager 304 preferentially. Therefore, the charge/discharge cycles of the external power storage device 4 can be reduced, and the life of the external power storage device 4 can be extended.

Furthermore, in a case where the controller 301 is not connected to the external apparatus 5 by the connector 308, the external power storage device 4 is attached to the power storage device attachment portion 307, the radiographic imager 304 is not performing imaging, and the remaining charge amount of the built-in power storage device 306 is less than a predetermined value, the controller 301 performs control such that electric power is supplied from the external power storage device 4 to the built-in power storage device 306. Therefore, when the remaining charge amount of the built-in power storage device 306 is low, it is possible to supply electric power from the external power storage device 4 to the built-in power storage device 306 to charge the built-in power storage device 306.

In a case where the controller 301 is not connected to the external apparatus 5 by the connector 308, the external power storage device 4 is attached to the power storage device attachment portion 307, and the radiographic imager 304 is operating in the moving image shooting mode, the controller 301 performs control such that electric power is supplied from the external power storage device 4 to the radiographic imager 304 preferentially. Therefore, in the moving image shooting mode in which power consumption is large, the external power storage device 4 can be used to secure the remaining charge amount of the built-in power storage device 306.

Further, in a case where the controller 301 is not connected to the external apparatus 5 by the connector 308 and the external power storage device 4 is not attached to the power storage device attachment portion 307, the controller 301 prohibits the radiographic imager 304 from operating in the moving image shooting mode. Therefore, it is possible to prevent the remaining charge amount of the built-in power storage device 306 from running out during imaging.

Furthermore, the controller 301 displays the remaining charge amount of the built-in power storage device 306 and/or the external power storage device 4 on the display part 303 provided on the housing 31 of the FPD cassette 3. Therefore, the user can recognize the remaining charge amount of the built-in power storage device 306 and/or the external power storage device 4.

Furthermore, in a case where the external power storage device 4 is not attached to the power storage device attachment portion 307, the controller 301 displays, on the display part 303 provided on the housing 31 of the FPD cassette 3, a message that the external power storage device 4 is not attached. Therefore, the user can recognize that the external power storage device 4 is not attached from the display of the console 1.

In a case where the information received from the FPD cassette 3 indicates that the remaining charge amount of the external power storage device 4 and the built-in power storage device 306 is equal to or lower than a predetermined value, the console 1 displays the fact on the display part 103 of the console 1. Therefore, the user can grasp that the remaining charge amount of the FPD cassette 3 has decreased from the display of the console 1.

Further, the console 1 displays the number of images that can be captured by imaging and/or the time period for which imaging can be performed corresponding to the remaining charge amount of the external power storage device 4 and the built-in power storage device 306 on the display part 103. Therefore, the user can grasp, from the display of the console 1, the number of images that can be captured by imaging and/or the time period for which imaging can be performed corresponding to the remaining charge amount of the FPD cassette 3.

Further, in a case where the external power storage device 4 is not attached to the power storage device attachment portion 307, the console 1 displays the fact on the display part 103 of the console 1. Therefore, the user can recognize that the external power storage device 4 is not attached from the display of the console 1.

Further, in a case where the external power storage device 4 is not attached to the power storage device attachment portion 307, the console 1 prohibits the user from making a selection operation to select the moving image shooting mode. Therefore, in a case where the external power storage device 4 is not attached, it is possible to prevent the user from selecting the moving image shooting mode in the console 1.

Note that the descriptions in the above embodiment are some preferred examples of the present invention, and the present invention is not limited thereto.

For example, in the above embodiment, the console 1 is integrated with a medical cart, but the console 1 is not limited to being mounted on the medical cart. Further, in the above embodiment, the FPD cassette 3 is used for imaging on rounds, but the FPD cassette 3 may be used for imaging in an imaging room.

Further, in the above, as a computer-readable medium of the programs according to the present invention, a hard disk, a semiconductor nonvolatile memory, or the like is used as an example, but the present invention is not limited to this example. As the computer-readable medium a portable recording medium, such as a CD-ROM, can be used. In addition, a carrier wave can be used as a medium for providing data of the programs according to the present invention via a communication line.

In addition, the detailed configuration and the detailed operation of each apparatus constituting the radiographic imaging system can be appropriately modified without departing from the scope of the present invention.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2023-079776, filed on May 15, 2023, including description, claims, drawings and abstract is incorporated herein by reference.

What is claimed is:

1. A radiographic imaging apparatus comprising:

a radiographic imager that performs imaging, thereby capturing a radiographic image;

a built-in power storage device that supplies electric power to the radiographic imager;

an attachment portion to which an external power storage device that supplies electric power to the radiographic imager is to be detachably attached;

a connector that is electrically connectable to an external apparatus; and a hardware processor that, in a case where the hardware processor is connected to the external apparatus by the connector and the radiographic imager is performing imaging, performs control to supply electric power supplied from the external apparatus to the radiographic imager, and in a case where the hardware processor is connected to the external apparatus by the connector and the radiographic imager is not performing imaging, performs control to supply the electric power supplied from the external apparatus to the built-in power storage device or the external power storage device attached to the attachment portion.

2. The radiographic imaging apparatus according to claim 1, wherein in the case where the hardware processor is connected to the external apparatus by the connector and the radiographic imager is not performing imaging, the hardware processor performs control to supply the electric power supplied from the external apparatus to the built-in power storage device preferentially, but performs control to supply the electric power supplied from the external apparatus to the external power storage device in a case where a remaining charge amount of the built-in power storage device is equal to or greater than a predetermined value.

3. The radiographic imaging apparatus according to claim 1, wherein the built-in power storage device is a lithium-ion capacitor, and the external power storage device is a lithium-ion battery.

4. The radiographic imaging apparatus according to claim 1, wherein in a case where the hardware processor is not connected to the external apparatus by the connector, the hardware processor performs control to supply electric power from the built-in power storage device or the external power storage device attached to the attachment portion to the radiographic imager.

5. The radiographic imaging apparatus according to claim 4, wherein in the case where the hardware processor is not connected to the external apparatus by the connector, the hardware processor performs control to supply electric power from the built-in power storage device to the radiographic imager preferentially in a case where the external power storage device is attached to the attachment portion.

6. The radiographic imaging apparatus according to claim 1, wherein in a case where the hardware processor is not connected to the external apparatus by the connector, the external power storage device is attached to the attachment portion, the radiographic imager is not performing imaging, and a remaining charge amount of the built-in power storage device is less than a predetermined value, the hardware processor performs control to supply electric power from the external power storage device to the built-in power storage device.

7. The radiographic imaging apparatus according to claim 1, wherein in a case where the hardware processor is not connected to the external apparatus by the connector, the external power storage device is attached to the attachment portion, and the radiographic imager is operating in a moving image shooting mode, the hardware processor performs control to supply electric power from the external power storage device to the radiographic imager preferentially.

8. The radiographic imaging apparatus according to claim 1, wherein in a case where the hardware processor is not connected to the external apparatus and the external power storage device is not attached to the attachment portion, the hardware processor prohibits the radiographic imager from operating in a moving image shooting mode.

9. The radiographic imaging apparatus according to claim 1, wherein the hardware processor displays a remaining charge amount of the built-in power storage device and/or the external power storage device on a display provided on a housing of the radiographic imaging apparatus.

10. The radiographic imaging apparatus according to claim 1, wherein in a case where the external power storage device is not attached to the attachment portion, the hardware processor displays a message that the external power storage device is not attached to the attachment portion on a display provided on a housing of the radiographic imaging apparatus.

11. A radiographic imaging system comprising:

the radiographic imaging apparatus according to claim 1; and a console that receives information indicating a state of the radiographic imaging apparatus.

12. The radiographic imaging system according to claim 11, wherein in a case where a remaining charge amount of the external power storage device and the built-in power storage device is equal to or less than a predetermined value, the console displays, on a display of the console, a message that the remaining charge amount of the external power storage device and the built-in power storage device is equal to or less than the predetermined value.

13. The radiographic imaging system according to claim 11, wherein the console displays, on a display of the console, a number of images that can be captured by imaging and/or a time period for which imaging can be performed, the number and the time period corresponding to a remaining charge amount of the external power storage device and the built-in power storage device.

14. The radiographic imaging system according to claim 11, wherein in a case where the external power storage device is not attached to the attachment portion, the console displays, on a display of the console, a message that the external power storage device is not attached to the attachment portion.

15. The radiographic imaging system according to claim 11, wherein in a case where the external power storage device is not attached to the attachment portion, the console prohibits a user from making a selection operation to select a moving image shooting mode.

16. The radiographic imaging apparatus according to claim 1, wherein in a case where the hardware processor is connected to the external apparatus by the connector and the radiographic imager is not performing imaging, performs control to supply the electric power supplied from the external apparatus directly to the built-in power storage device or the external power storage device attached to the attachment portion.

17. The radiographic imaging apparatus according to claim 1, further comprising a switch that is controlled by the hardware processor such that the hardware processor determines if the radiographic imager is performing imaging and controls the supply of the electric power supplied from the external apparatus based on whether or not the radiographic imager is performing imaging.

* * * * *